(12) United States Patent
Lasser et al.

(10) Patent No.: US 6,971,991 B2
(45) Date of Patent: Dec. 6, 2005

(54) APPARATUS FOR MULTIMODAL PLANE WAVE ULTRASOUND IMAGING

(75) Inventors: Robert S. Lasser, Washington, DC (US); Marvin E. Lasser, Potomac, MD (US); John W. Gurney, Great Falls, VA (US)

(73) Assignee: Imperium, Inc., Silver Spring, MD (US)

( * ) Notice: Subject to any disclaimer, the term of this patent is extended or adjusted under 35 U.S.C. 154(b) by 136 days.

(21) Appl. No.: 10/382,866

(22) Filed: Mar. 7, 2003

(65) Prior Publication Data

US 2003/0181801 A1 Sep. 25, 2003

Related U.S. Application Data

(60) Provisional application No. 60/362,541, filed on Mar. 8, 2002.

(51) Int. Cl.[7] .................................... A61B 8/00
(52) U.S. Cl. ........................................ 600/437
(58) Field of Search ................ 600/407–472; 128/916, 898; 73/602–633; 367/7, 11, 130, 138

(56) References Cited

U.S. PATENT DOCUMENTS

| | | | |
|---|---|---|---|
| 4,434,661 A | * | 3/1984 | Miwa et al. ............... 73/625 |
| 4,651,744 A | | 3/1987 | Bristow et al. |
| 5,231,573 A | * | 7/1993 | Takamizawa ............ 600/437 |
| 5,474,072 A | | 12/1995 | Shmulewitz |
| 5,479,927 A | | 1/1996 | Shmulewitz |
| 5,483,963 A | | 1/1996 | Butler et al. |
| 5,662,109 A | | 9/1997 | Hutson |
| 5,664,573 A | | 9/1997 | Shmulewitz |
| 5,776,062 A | | 7/1998 | Nields |
| 5,938,613 A | | 8/1999 | Shmulewitz |
| 5,983,123 A | | 11/1999 | Shmulewitz |
| 6,006,126 A | | 12/1999 | Cosman |
| 6,102,866 A | | 8/2000 | Nields et al. |
| 6,236,875 B1 | | 5/2001 | Bucholz et al. |
| 6,254,538 B1 | | 7/2001 | Downey et al. |
| 6,302,579 B1 | | 10/2001 | Meyer et al. |
| 6,334,847 B1 | | 1/2002 | Fenster et al. |
| 6,342,891 B1 | | 1/2002 | Fenster et al. |
| 6,552,841 B1 | | 4/2003 | Lasser et al. |

\* cited by examiner

*Primary Examiner*—Ali Imam
(74) *Attorney, Agent, or Firm*—Burns, Doane, Swecker & Mathis, L.L.P.

(57) ABSTRACT

An ultrasonic imaging apparatus combined with an x-ray imaging apparatus and/or an additional ultrasonic imaging apparatus performs ultrasonic sonography and/or x-ray imaging or multiple ultrasonic sonography to produce imagery that are spatially correlated. A holding means holds an object to be imaged in compression in an examination area. The x-ray source and the ultrasonic source are each relocatable from an inactive imaging position to an inactive non-imaging position. The x-ray image and ultrasonic sonography image are both taken in transmission and the resulting images contain a registry object to assist a user in spatially correlating the images. The speckle contained in the sonography image is reduced allowing for higher resolution of abnormalities in the tissue and improved concurrent biopsy procedures.

62 Claims, 9 Drawing Sheets

APPARATUS FOR MULTIMODAL PLANE WAVE ULTRASOUND IMAGING

CROSS-REFERENCE TO RELATED APPLICATIONS

The present application claims the priority under 35 U.S.C. §119 of U.S. Provisional Application No. 60/362,541, filed in the United States of America on Mar. 8, 2002, the entire contents of which are hereby incorporated herein by reference.

BACKGROUND

Imaging technologies for medical purposes generally image either hard tissue or soft tissue. For example, hard tissue, i.e., bones and teeth, or radio opaque enhanced features, i.e., gastrointestinal features, circulatory features, and so forth, can be imaged by x-ray technologies. Soft tissue, i.e., muscles, fat, and other fleshy portions, can be imaged by ultrasonic technologies.

X-ray technology for providing images of tissue include the use of x-rays for the imaging of female breasts, i.e., x-ray mammography. Typically, a female breast is placed in position to be exposed by the x-ray source with a resulting image captured by an x-ray detector or x-ray film. Differences in the transmission of the x-ray energy through the tissue are captured and resolved to indicate areas of diagnostic concern. These areas of concern are then further investigated by a separate application of ultrasonic techniques. For example, if a mammographic x-ray image indicates an area of suspicion in the tissue, the patient is scheduled for a later ultrasonic technique to gather additional soft tissue information. This practice can be time consuming, inconvenient to the patient, and produces uncorrelated images which hamper accurate diagnosis.

Examples of a combined x-ray imagery and ultrasound sonography apparatus is disclosed, for example, in U.S. Pat. No. 5,664,573. As disclosed in the '573 patent, an x-ray mammography apparatus is positioned orthogonally to an ultrasonic sonography apparatus. A transmission image of tissue is obtained with the x-ray apparatus while a reflective image of the tissue parallel to the that of the x-ray plane is obtained with the sonography apparatus. Subsequent to the imaging of the tissue, the mammography image and the sonography image are reconstructed by processing the respective image data.

An alternative approach to combining medical diagnostic techniques is disclosed in U.S. Pat. No. 6,302,579 B1. In the '579 patent, a large scale, i.e., room scale, examination arrangement positions a patient on an examination table, which is then manipulated through multiple imaging stations, such as a magnetic resonance system, a CT system, and an angiography system. The rotation of the patient is accomplished by a common rotary table. However, a large multi-station diagnostic room does not address the difficulties with obtaining correlated images of the patient.

SUMMARY

The present invention is directed to a multimode imaging apparatus that combines an ultrasonic imaging apparatus with another imaging apparatus to collect and produce imagery that is spatially correlated to obtain refined position information or stereo imaging. An ultrasonic imaging apparatus can be combined with an x-ray imaging apparatus to obtain ultrasonic imagery and x-ray imagery or with another or multiple ultrasonic imaging apparatus in the same or different operating mode to obtain multiple ultrasonic imagery in transmission and/or reflection.

Exemplary embodiments are directed to an apparatus for ultrasonic imaging of an object. In an exemplary embodiment, the apparatus for ultrasonic imaging of an object has a means for holding an object to be imaged in compression in an examination area, an ultrasonic source located on a first side of the examination area, and an ultrasonic detector located on a second side of the examination area for receiving ultrasonic energy transmitted from the ultrasonic source through the object. In an aspect of the apparatus for ultrasonic imaging of an object, the ultrasonic source is movable from a first active position to a second active position, and the apparatus comprises an x-ray source relocatable to the first active position and an x-ray detector on the second side of the examination area that receives x-ray energy generated by the x-ray source and propagated transmissively through the object to the x-ray detector.

In an additional exemplary embodiment, an apparatus for multi-mode imaging of an object has a means for holding the object in an examination area, an ultrasonic source, an x-ray source, a means for matching the ultrasonic source and the x-ray source and for relocatably positioning either one of the ultrasonic source and the x-ray source at an imaging position on a first side of the examination area, an ultrasonic detector located on a second side of the examination area for receiving ultrasonic energy transmitted from the ultrasonic source at the imaging position through the object, and an x-ray detector located on the second side of the examination area for receiving x-ray energy transmitted from the x-ray source at the imaging position through the object. In an aspect of the apparatus for multi-mode imaging of an object, the apparatus has a registry object and a field of view of the ultrasonic source and the x-ray source when each of the sources is positioned at the imaging position. The registry object is non-transmissive to both the ultrasonic energy and the x-ray energy.

In an exemplary embodiment, a method of imaging an object with an apparatus for multi-mode imaging holds an object to be imaged in an examination position, moves an x-ray source to an imaging position on a first side of the object such that x-ray energy transmits through at least a portion of the object to an x-ray detector, captures an x-ray image of the portion of the object with the x-ray detector, moves the x-ray source to a non-imaging position, moves an ultrasonic source to the imaging position such that ultrasonic energy transmits through the portion of the object to an ultrasonic detector, captures an ultrasonic image of the portion of the object with the ultrasonic detector, and spatially correlates the portion of the object in the x-ray image with the portion of the object in the ultrasonic image. In an aspect of the method, the x-ray image and the ultrasonic image each contain at least one registry object used in spatially correlating the ultrasonic image and the x-ray image. In an additional aspect, the method evaluates the spatially correlated images and diagnoses a medical condition.

An exemplary apparatus for multimode imaging an object to obtain images in at least two ultrasonic imaging modes comprises a first ultrasonic imaging transducer, a second ultrasonic imaging transducer, and an ultrasonic detector. The first ultrasonic imaging transducer, the second ultrasonic imaging transducer, and the ultrasonic detector are arranged about an imaging area. The first ultrasonic imaging transducer is colinear with the imaging area and the ultrasonic detector along a first beam axis to transmit a first ultrasonic energy from the first ultrasonic imaging transducer through the imaging area to the ultrasonic detector. The second ultrasonic imaging transducer transmits a second ultrasonic energy from the second ultrasonic imaging transducer into the imaging area along a second beam axis, the first beam axis orthogonal to the second beam axis.

In one exemplary aspect, the apparatus includes a beam splitter and the second ultrasonic energy interacts with the beam splitter to propagate at least a portion of the second ultrasonic energy coaxially to the first ultrasonic energy into the imaging area and the second ultrasonic energy reflects to the ultrasonic detector.

An exemplary apparatus for multimode imaging an object to obtain images in at least two ultrasonic imaging modes comprises a first ultrasonic imaging transducer operating in a transmission mode, a second ultrasonic imaging transducer operating in a pulse echo mode, and an ultrasonic detector. The first ultrasonic imaging transducer, the second ultrasonic imaging transducer, and the ultrasonic detector are arranged about an imaging area. The first ultrasonic imaging transducer is colinear with the imaging area and the ultrasonic detector along a first beam axis to transmit a first ultrasonic energy from the first ultrasonic imaging transducer through the imaging area to the ultrasonic detector. The second ultrasonic imaging apparatus is colinear with the imaging area and the ultrasonic detector along the first beam axis to transmit a second ultrasonic energy from the second ultrasonic imaging transducer into the imaging area, the second ultrasonic energy reflected to the ultrasonic detector. In one exemplary aspect, the second ultrasonic imaging apparatus includes an annular transducer.

An exemplary apparatus for multimode imaging an object from a plurality of imaging positions to obtain stereo images comprises means for positioning an object in an examination area, a plurality of imaging positions for an ultrasonic source, a plurality of detector positions for an ultrasonic detector, and an acoustic coupling between the examination area, the plurality of imaging positions and the plurality of detector positions. Each imaging position is colinear with the examination area and one of the plurality of detector positions along a beam axis.

BRIEF DESCRIPTION OF THE DRAWINGS

Objects and advantages of the invention will become apparent from the following detailed description of preferred embodiments in connection with the accompanying drawings, in which like numerals designate like elements and in which.

DETAILED DESCRIPTION OF THE PREFERRED EMBODIMENTS

Figure 1:
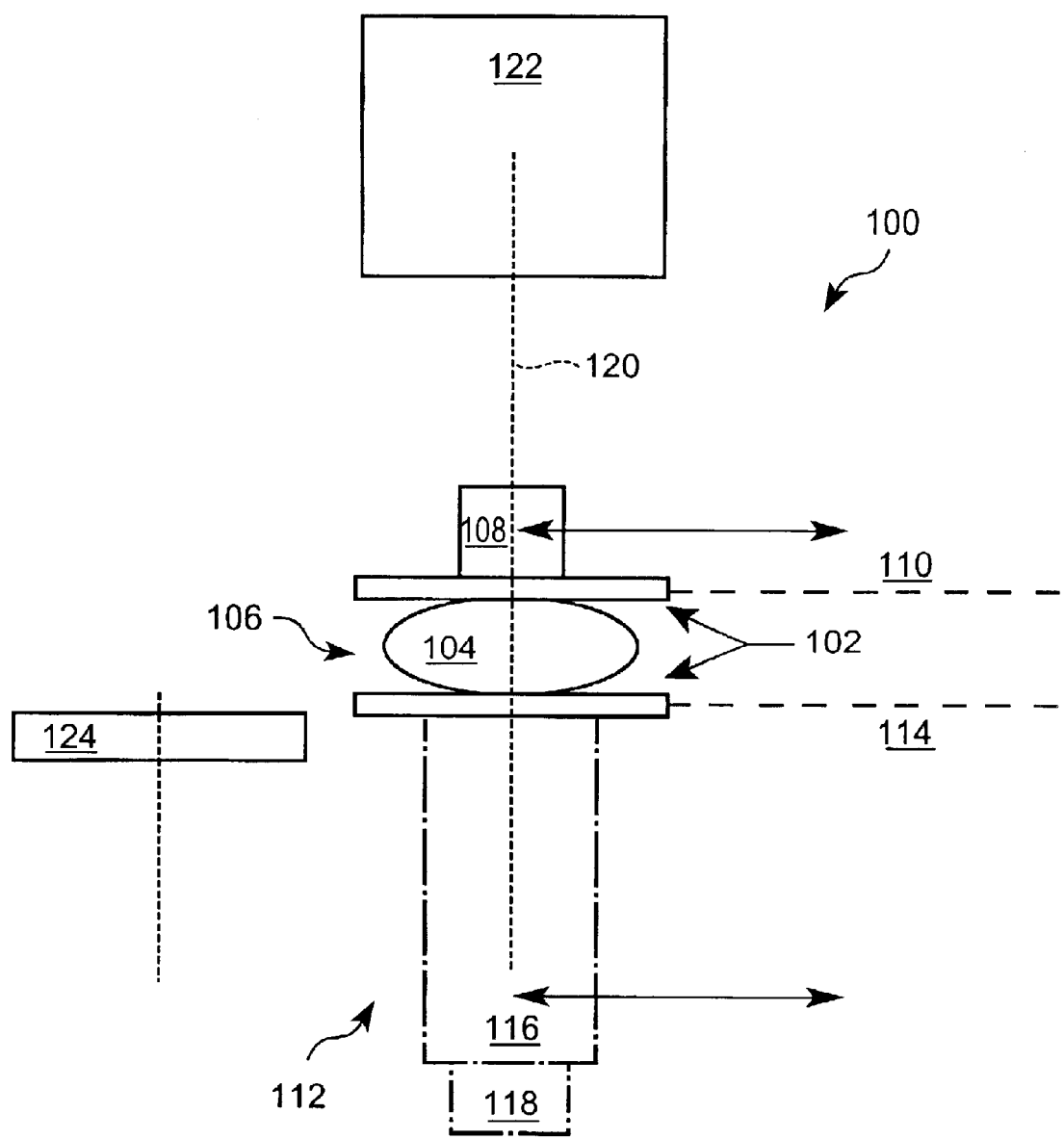
FIG. 1 is an exemplary embodiment of an apparatus for multimode imaging of an object in which an ultrasonic imaging apparatus is combined with an x-ray imaging apparatus.

An exemplary apparatus for multimode imaging of an object is illustrated in FIG. 1 as an apparatus 100. The FIG. 1 apparatus 100 includes means for holding 102 an object 104 to be imaged in compression in an examination area 106, a first ultrasonic source 108 located on a first side 110 of the examination area 106, and a first ultrasonic detector 112 located on a second side 114 of the examination area 106 for receiving a first ultrasonic energy transmitted from the first ultrasonic source 108 through the object 104.

In an exemplary embodiment, the holding means is made of any suitable ultrasonic transmissive material. Further, the holding means provides ultrasonic coupling to the object. The ultrasonic coupling can be assisted and/or enhanced by the use of a coupling aid, such as an ultrasonic gel. The holding means preferably holds the object stationary during the duration of the imaging operation. As an example and as shown in FIG. 1, the holding means can be compression plates that are used to hold the object to be imaged in compression in the examination area. The compression plates can be movable, i.e., translated or rotated, such that opposing surfaces of a pair of compression plates can be brought together to hold the object in compression therebetween. Although compression of the object is not required for sonography, holding the object in compression minimizes movement of the object during the sonography procedure and any prior or subsequent imaging procedures, i.e., reflective ultrasonic imagery (including B-scan ultrasound and pulse echo ultrasound), x-ray imaging, x-ray mammography, and so forth. Further, the compression plates can aid in maintaining the colinearity of the imaging sources and receivers/detectors, i.e., during imaging, the sources are maintained in a linear relationship along a beam axis from the source through the object to the detector for transmission imaging modes. In addition to compressive plates, the holding means can be a cup, cuff, ring or receiving element that can receive the object to be imaged, such as a female breast, an arm, a portion of or the entire torso of a person, or an animal. The holding means can be enhanced by for example, vacuum or suction technology that assists in drawing the tissue into the holding means.

The first ultrasonic source is located on a first side of the examination area. In an exemplary embodiment, a first ultrasonic source is a large unfocused source that operates in the kilohertz to megahertz range for through transmission (also called C-scan ultrasound). An example of through transmission ultrasound is disclosed in commonly owned U.S. patent application Ser. No. 09/479,598, entitled "ULTRASONIC IMAGER" and filed on Jan. 7, 2000, the entire contents of which are incorporated herein by reference. The first ultrasonic source projects ultrasonic energy in a transmission mode through the object to a second side of the examination area. Further, the first ultrasonic source can be an ultrasonic transducer that couples through the holding means to the object to be imaged. For example, one of the compressive plates, i.e., the compressive plate on the first side of the examination area, can have an opening formed in the compressive plate's planar surface and into which the first ultrasonic source is fitted. The first ultrasonic source can then contact and/or ultrasonically couple to the object positioned in the examination area, i.e., the first ultrasonic source or a portion of the first ultrasonic source is fitted into the opening with the transducer exposed to and/or facing the examination area, such that ultrasonic energy can propagate to the object. An example of a suitable ultrasonic source is provided in commonly owned U.S. patent application Ser. No. 09/479,598, entitled "ULTRASONIC IMAGER" and filed on Jan. 7, 2000, the entire contents of which are incorporated herein by reference.

The first ultrasonic detector located on the second side of the examination area receives the first ultrasonic energy transmitted through the object. In an exemplary embodiment, the first ultrasonic detector 112 is coupled to the holding means 102, i.e., ultrasonically coupled to or integrated with one of the coupling plates. The first ultrasonic detector can be an ultrasonic receiver transducer, an ultrasonic camera, or other suitable detector that detects ultrasonic energy and converts the ultrasonic energy into an image. In an exemplary embodiment, the first ultrasonic detector can be an ultrasonic camera. FIG. 1 shows a first ultrasonic detector 112 having a camera body 116 and a camera electronics housing 118. The camera body 116 can contain the optical elements for the detector 112 and is interfaced to the camera electronics that are located in a camera electronics housing 118. The camera body 116 can include optical elements such as lenses, ultrasonic coupling medium, i.e., water, a detector array, i.e., a means for converting ultrasonic energy to electrical energy, and other ultrasonic optical elements for receiving and transmitting the ultrasonic energy to the camera electronics housing 118. In an exemplary embodiment, a lens of the camera body protrudes through holding means, i.e., protrudes through the lower plate of the coupling plates, and ultrasonically couples to the object to be imaged. In an exemplary embodiment, the camera body can be, for example, a three-inch diameter housing which focuses the ultrasonic energy on the detector array contained in the camera electronics housing.

In one aspect, the apparatus includes at least a second ultrasonic source and a second ultrasonic detector. The second ultrasonic source can be suitably located depending on the ultrasonic mode, e.g., transmission or reflection, to receive a second ultrasonic energy transmitted from the ultrasonic source. For example, the second ultrasonic source operating in transmission mode can be located to receive a second ultrasonic energy transmitted from the second ultrasonic source through the object. A second beam axis between the second ultrasonic source and the second ultrasonic detector is angularly separated from a first beam axis between the first ultrasonic source and the first ultrasonic detector. Further, the first ultrasonic source and the first ultrasonic detector can be rotated about the examination area while the first beam axis between the first ultrasonic source and the first ultrasonic detector intersects at least a portion of the examination area, e.g., the first ultrasonic source and the first ultrasonic detector can be rotated in tandem. In this aspect, the apparatus is operating substantially similar to a computed tomography apparatus, collecting ultrasonic images of an object in the examination area from multiple angles.

In another example, the apparatus includes at least a second ultrasonic source operating in a pulse echo mode. An example of a second ultrasonic source operating in a pulse echo mode includes a beam splitter located in the first beam axis between the first ultrasonic source operating in a transmission mode and the first ultrasonic detector. The second ultrasonic source transmits a second ultrasonic energy to the beam splitter in a direction orthogonal to the first beam axis and the second ultrasonic energy is split by the beam splitter and directed into the examination area. The beam splitter acts to both reflect and transmit portions of the acoustic energy that falls upon it. A suitable beam splitter can be a thin piece of flat metal. Additional suitable beam splitters and additional information on ultrasonic equipment utilizing a beam splitter is disclosed in commonly owned U.S. patent application Ser. No. 09/479,598, entitled "ULTRASONIC IMAGER" and filed on Jan. 7, 2000, the entire contents of which are incorporated herein by reference. In an exemplary aspect, the first ultrasonic detector simultaneously receives a transmitted signal from the first ultrasonic source and a reflected signal from the second ultrasonic source. Other examples of a second ultrasonic source operating in a pulse echo mode can be used, including direct coupling of the ultrasonic source operating in a pulse echo mode to the object. U.S. Pat. No. 5,664,573, the entire contents of which are incorporated herein by reference, discloses directly imaging a female breast with B-scan ultrasound by an ultrasonic source positioned on a common axis with the breast, e.g., without a beam splitter.

In the above described first aspect, the second ultrasonic source and the second ultrasonic detector can be substantially similar to those described herein with respect to the first ultrasonic source, except that the second ultrasonic source can operate in pulse echo mode to obtain a reflected image from the object in the examination area. Other examples of suitable ultrasonic sources include those disclosed in commonly owned U.S. patent application Ser. No. 09/479,598, entitled "ULTRASONIC IMAGER" and filed on Jan. 7, 2000, the entire contents of which are incorporated herein by reference.

Figure 2:
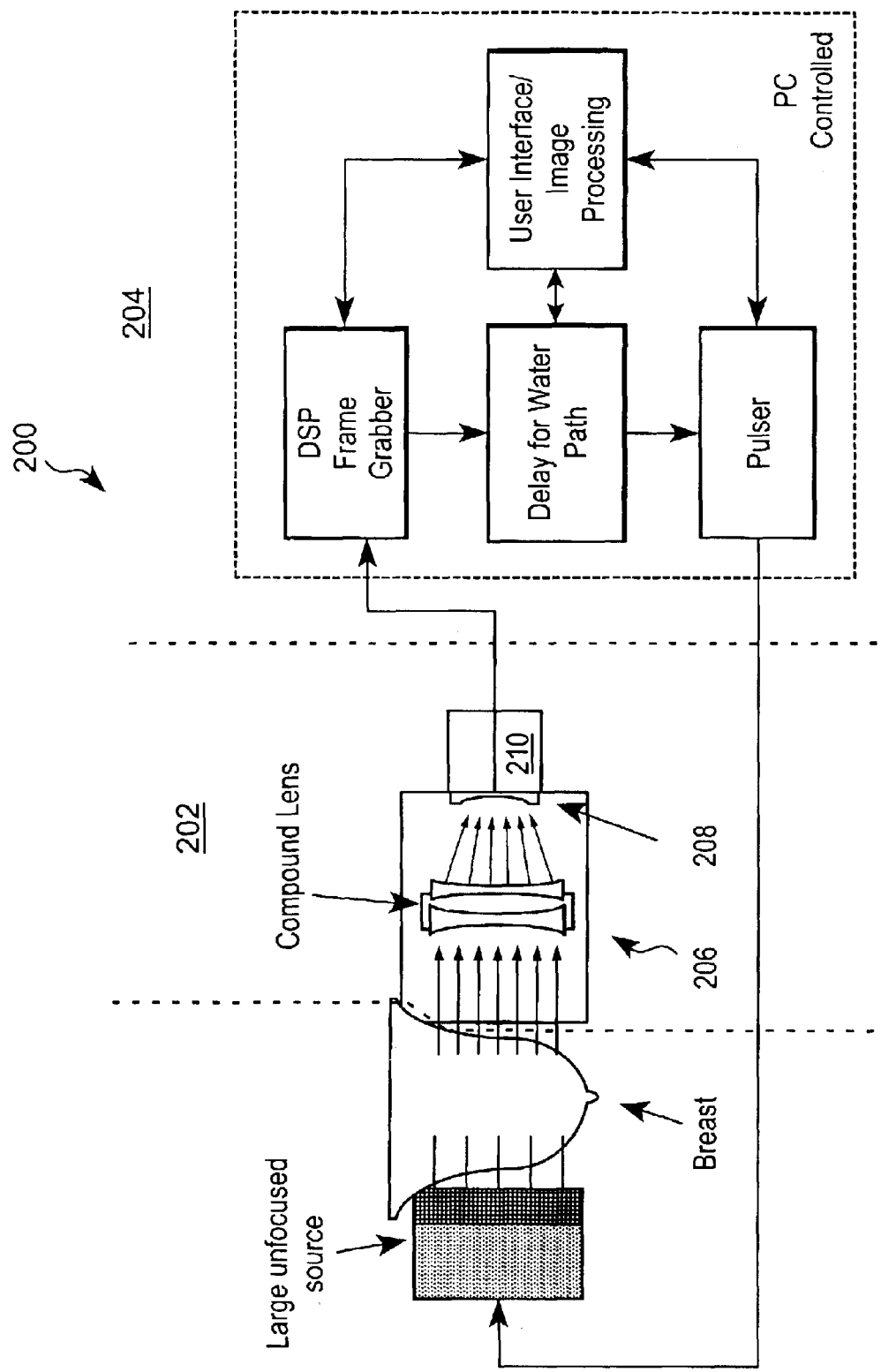
FIG. 2 shows a schematic diagram of an ultrasonic camera with an image capturing portion and shows a flow diagram of the electronic signal processing.

FIG. 2 shows a schematic diagram of an ultrasonic camera 200 with an image capturing portion 202. A flow diagram of the electronics 204 represents the electronic signal processing, at least some of which can occur in the camera electronics housing. Any suitable electronics for sourcing and detecting ultrasound can be used, such as that disclosed in U.S. Pat. No. 5,483,963, the entire contents of which are herein incorporated by reference, a field programmable gate array or other digital signal processor. In the image capturing portion 202, unfocused energy transmitted through the object, i.e., depicted as a breast but any suitable object can be imaged including other portions of a human or an animal, from a large unfocused ultrasonic source is received by optical elements 206. The optical elements 206 can be an acoustic lens, such as the compound lens shown in FIG. 2. The unfocused ultrasonic energy is focused by the optical elements 206 onto a 2D array 208. The 2D array 208 is connected to an interface electronics module 210 and converts the acoustic energy into an electrical signal that is processed by the electronics 204 to produce an image. The image can be presented to a user on a video monitor, a LCD screen, or a printed copy.

A suitable 2D array is a two-dimensional transducer integrated circuit, such as that disclosed in U.S. Pat. No. 5,483,963, the entire contents of which are herein incorporated by reference. The array can be, for example, a 120×120 pixel array which can produce electronic signals corresponding to the received ultrasonic energy. For example, piezoelectric elements can be used as the 2D array.

In FIG. 1, the ultrasonic source 108 is movable from a first active position to a second inactive position. In the first active position, the beam axis 120 of the source 108 is placed in line with the beam axis 120 of the camera body. The beam axis 120 intersects with an examination area 106 of the object 104 to be imaged.

In an exemplary embodiment represented in FIG. 1, the apparatus 100 has a second imaging source, such as an x-ray source 122, mounted to be in line with the beam axis 120 at an active position and an x-ray detector 124 on the second side 114 of the examination area 106. The x-ray source 122 can be permanently mounted or can be removable, e.g., the x-ray source can be relocatable from the first active position. The x-ray detector 124 can be repositioned to be in line with the beam axis 120 of the x-ray source 122 in the active position. The x-ray detector 124 on the second side 114 of the examination area 106 receives x-ray energy generated by the x-ray source 122 and propagated transmissively through the object 104 to the x-ray detector 124 along the beam axis 120. Accordingly, by having a source that is movable from a first active position to a second inactive position, and vice versa, an image of the object can be generated without moving the object.

The x-ray detector can be any suitable x-ray detector. For example, the x-ray detector can be x-ray sensitive film. Alternatively, the x-ray detector can be a digital x-ray detector which captures x-ray energy and translates that energy into digitized data for manipulation by a computer means or software means.

An ultrasonic imaging apparatus can project ultrasound energy from a transducer through an object to be imaged, such as a patient's breast, where it falls upon an ultrasonic detector, such as a transducer camera. In addition, the ultrasonic imaging apparatus can be coupled with a second mode of imaging, such as an x-ray imaging apparatus, to provide multi-mode functionality, i.e., the ability to obtain an image of an object using more than one energy technique, such as x-ray imaging and ultrasonic sonography or transmissive and reflective sonography.

Figure 3:
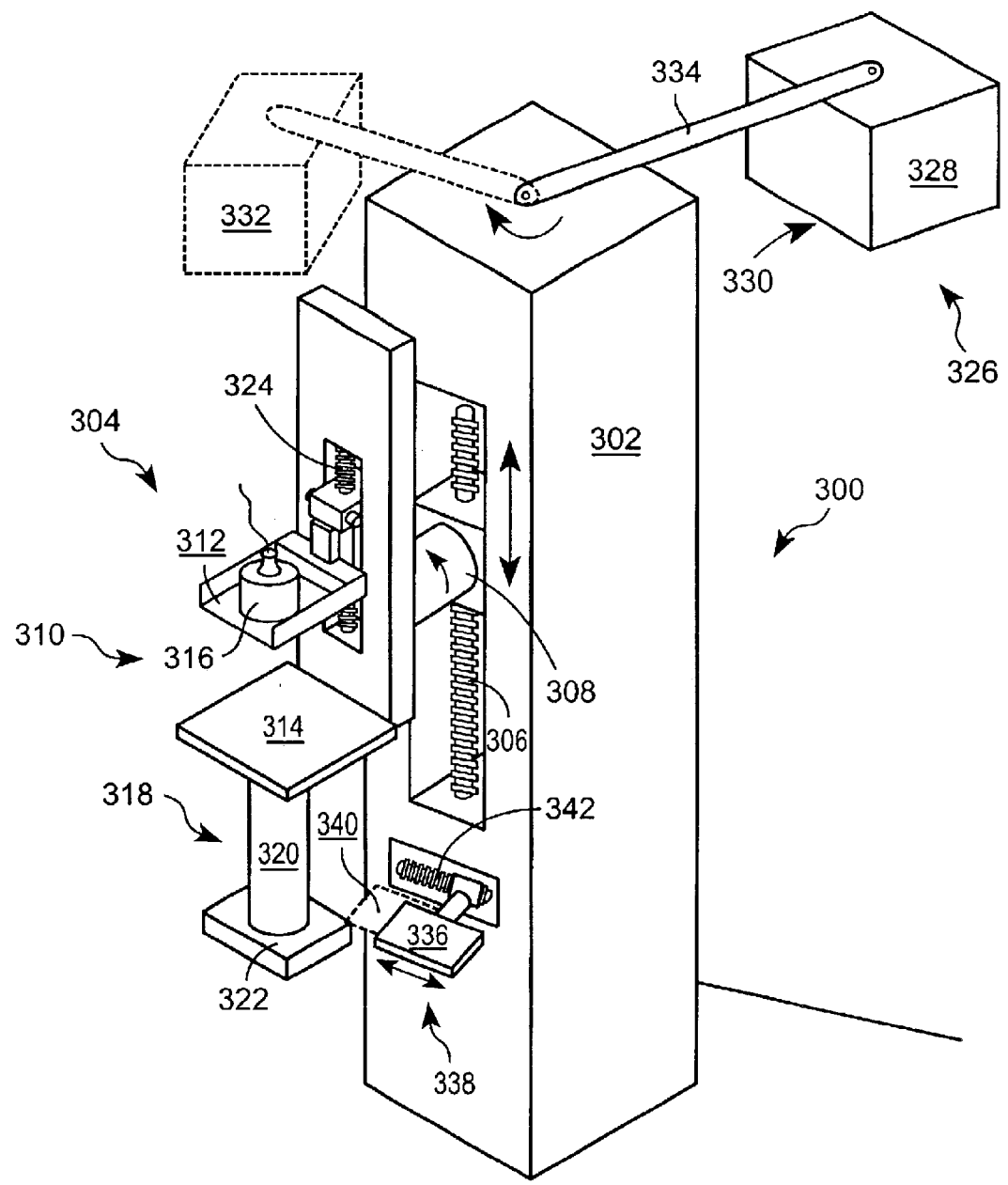
FIG. 3 is an exemplary embodiment of an apparatus for multi-mode imaging of an object in which an ultrasonic imaging apparatus is combined with an x-ray imaging apparatus.

In an exemplary implementation of a multi-mode imaging apparatus, a conventional x-ray machine, such as an x-ray mammography machine or any other x-ray machine, is adapted to hold ultrasound components as illustrated in FIG. 3 as apparatus 300. The FIG. 3 apparatus 330 includes a translation housing 302 and an axially mounted sonography imaging apparatus 304. Freedom of movement in both the vertical and the horizontal direction and a rotational degree of freedom is provided by a rail-like system 306, i.e., engaging teeth although other translational systems can be used such as a screw-type system, jack screw and so forth, and the arm 308. Additional positioning is provided by the use of a holding means 310 for holding the object in an examination area, i.e., opposing movable plates 312, 314. The holding means 310 includes an ultrasonic source 316, such as a three-inch or one-inch ultrasonic transducer. For example, the ultrasonic source 316 is mounted in the upper plate 312 and has a surface flush with the contact surface for the object. In operation, this contact surface is ultrasonically coupled to the object and can be enhanced in its coupling efficiency by the use of an appropriate ultrasonic gel, or other coupling medium. A lower plate 314 is ultrasonically transmissive and is ultrasonically coupled to the detector 318. The detector is shown having a camera body 320 and a camera electronics housing 322.

In the exemplary embodiment shown in FIG. 3, the upper plate 312 can translate in the vertical direction on a secondary rail system 324. Alternatively, other portions of the ultrasonic imaging apparatus 304 can translate to provide translational freedom of the holding means 310 about the object to be imaged.

The apparatus 300 can have an associated x-ray imaging apparatus 326, such as an x-ray mammography apparatus, although other imaging apparatus can also be associated with the apparatus. An x-ray source 328 can be associatively mounted on the translation housing 302 in an inactive position 330, i.e, not in the beam axis for imaging the object. The x-ray source 328 can be relocated to the active position 332 to provide the x-ray source 328 for x-ray imaging. For example, the x-ray source 328 can be mounted to a rotation arm 334 that is rotated to place the x-ray source 328 at the active position 332. Concurrently, an x-ray detector, represented by x-ray detector 336, can be relocated from an inactive position 338 to the an active position 340. For example, x-ray detector 336 can be translated on tertiary rail system 342 to the active position 340.

In an exemplary embodiment, the x-ray imaging apparatus 326 can be mounted on moveable arms so that the apparatus can be moved and/or rotated about an object, such as a breast, an arm, a portion of the torso or limbs or the entire torso or limb of a person, or an animal such as a small animal, to obtain different views.

Changing the apparatus 300 from ultrasonic sonography apparatus 304 to x-ray imaging apparatus 326 can be accompanied by, for example, removal of the transducer from the upper plate and removal of the ultrasonic detector from the lower plate, thus preventing these components from being exposed in the x-ray imaging procedure and obstructing the field of view.

In addition to the above description of an ultrasonic sonography apparatus and a x-ray imaging apparatus, the apparatus 300 can also include, in addition to or in substitution for the x-ray imaging apparatus, one or more additional ultrasonic sonography apparatus having an ultrasonic source and an ultrasonic detector substantially similar to the second ultrasonic source and second ultrasonic detector described herein with respect to the exemplary embodiment of FIG. 1. Further, the additional ultrasonic sonography apparatus can operate in transmission or pulse echo mode and can be rotatable about an object to obtain multiple images of an object from different angular orientations for reconstruction into a stereo image, similar to a computed tomography apparatus.

Figure 4:
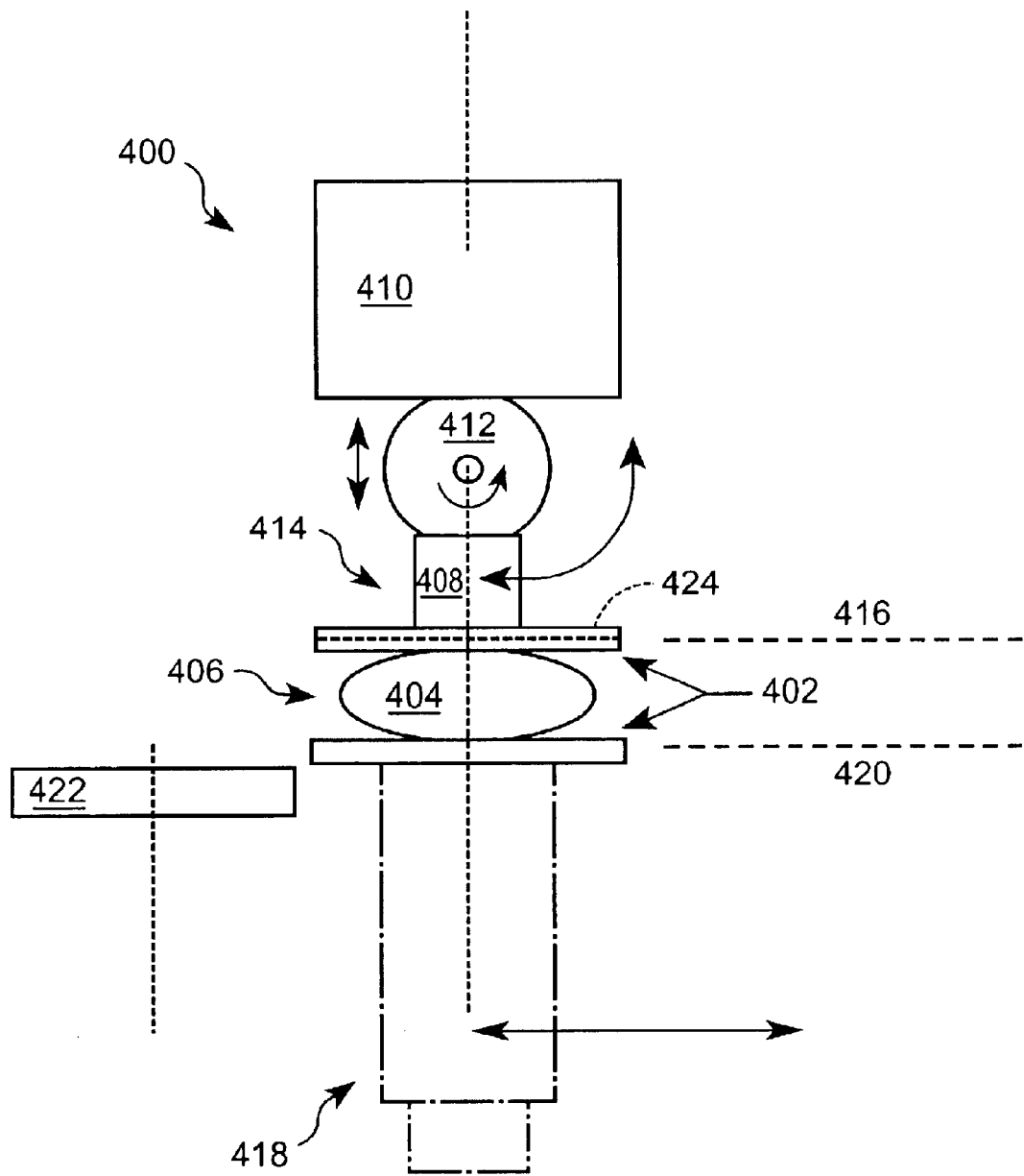
FIG. 4 is an additional exemplary embodiment of an apparatus for multi-mode imaging of an object in which an ultrasonic imaging apparatus is combined with an x-ray imaging apparatus.

An additional exemplary apparatus for multi-mode imaging of an object is illustrated in FIG. 4 as an apparatus 400. The FIG. 4 apparatus 400 includes a means for holding 402 the object 404 in an examination area 406, an ultrasonic source 408, an x-ray source 410, a means for mounting 412 the ultrasonic source 408 and the x-ray source 410 and for relocatably positioning either one of the ultrasonic source 408 and the x-ray source 410 in an imaging position 414 on a first side 416 of the examination area 406, an ultrasonic detector 418 located on a second side 420 of the examination area 406 for receiving ultrasonic energy transmitted from the ultrasonic source 408 at the imaging position 414 through the object 404, and an x-ray detector 422 located on the second side 420 of the examination area 406 for receiving x-ray energy transmitted from the x-ray source 410 at the imaging position 414 through the object 404.

Exemplary means for holding the object comprise materials that are transmissive to ultrasonic energy generated by the ultrasonic source and transmissive to x-ray energy generated by the x-ray source. For example, the holding means can be a pair of ultrasonic and x-ray transmissive plates. In addition, the holding means can be a compressive means such as a translational plate, clamp, suction cup, or other suitable means that is transmissive to x-rays and ultrasound.

An exemplary multi-mode imaging apparatus has a registry object in a field of view of the ultrasonic source and in the field of view of the x-ray source when each of the sources is respectfully at the imaging position. For example, the holding means can have on a surface or embedded within, a registry object or objects which are non-transmissive to both ultrasound and x-ray energies. Other examples of suitable registry objects include an embedded grid within the holding means, i.e., a grid embedded within the compressive plates, a mark, a crosshairs, or at least one other aligning element such as a user-positioned geometric figure. A registry object is represented in FIG. 4 as registry object 424 in the form of a grid embedded in the upper plate of the holding means 402.

The registry object is non-transmissive and/or reflective to both ultrasonic energy and x-ray energy. Accordingly, when exposed within the field of view of the detector, the registry object provides a reference point which can be used later to align spatially successive images taken of a single object when the object has not been moved between exposures. Preferably, the registry object is outside the portion of the field of view in which the object to be imaged is positioned. Thus, the registry object does not interfere with the transmission of the ultrasonic energy or the x-ray energy and does not interfere with the ability of the apparatus to obtain a complete image of the object. For example, the outer periphery of the field of view can be a border of non-transmissive material which provides the registry object.

In an exemplary embodiment, the imaging source, i.e., either the ultrasonic imaging source or the x-ray imaging source, is positioned at an imaging position of the apparatus. The imaging position is that position in which the beam axis from the source to the detector transmits the energy through the object to be imaged. Both the x-ray source and the ultrasonic source are mounted on a common housing.

For example, as shown in FIG. 4, the ultrasound source 408 and the x-ray source 410 may be mounted to a common mounting means 412. The mounting means rotates clockwise and/or counterclockwise around an axis to place either the ultrasound source or the x-ray source at the imaging position. In addition to rotation translation, the mounting means can be translated horizontally or vertically to provide clearance for the rotation motion and/or to provide the appropriate movement of the x-ray source or the ultrasound source to couple to the object and/or holding means in the imaging position, if desired.

In another example, the x-ray source may be fixed on the beam axis and the ultrasound source may be slid into place coupled to the object to be imaged. Alternative means by which to free the beam axis may also be used, including rotation in one of several planes, translational movement, or combinations of the two.

In these embodiments, the object to be imaged can remain stationary at an imaging position during the relocatable positioning of the ultrasonic source and the second imaging source, e.g., the x-ray source or other imaging source.

In addition to the x-ray source and the ultrasonic source being relocatably positioned, the corresponding ultrasonic detector or x-ray detector can be repositioned along the beam axis as appropriate to obtain a desired image. Accordingly, the detectors may be manipulated in their position in tandem to the manipulation of the sources, independent to the manipulation of the sources, and/or permanently positioned such as in an embodiment where the x-ray source is permanently positioned.

Ultrasonic energy captured by the ultrasonic detector forms an image from a plane within the object which is perpendicular to a path extending from the ultrasonic source to the ultrasonic detector. Accordingly, the detector, i.e., the two-dimensional transducer integrated circuit, converts the ultrasound energy into a two-dimensional picture analogous to how a video camera converts light into a 2-D visual image. Lack of uniformity in the object imaged will transmit the energy differently and result in a non-uniform ultrasound image. Such images can be interpreted to detect abnormalities such as cysts, that may be indicative of diseased tissue, such as cancer.

As with a video camera, the lenses in the camera can be moved to effect focusing at different depths through the object. The ability to focus can also allow a better determination of the location of any suspicious areas in the imaged object. An example of focusing of an ultrasound camera is disclosed in commonly owned U.S. patent application Ser. No. 09/479,598, entitled "ULTRASONIC IMAGER" and filed on Jan. 7, 2000, the entire contents of which are incorporated herein by reference.

In an exemplary embodiment of the ultrasonic source and detector, a large field of view may be used, i.e., three inches or greater. A larger field of view provides more context but at a loss of resolution. Alternatively, a small field of view, i.e., one inch or less, can provide a higher resolution but with less context.

In an exemplary embodiment, a 120×120 array is used as the detector. Accordingly, a three-inch field of view detector mapping to the array results in approximately 6× magnification. Similarly, a one-inch field of view maps to an approximately 2× magnification. Accordingly, the 2× magnification provides improved pixel to image ratio and can increase the quality of the ultrasonic image. This can be understood by a review of the ultrasonic image technology. The ultrasonic energy (V) is provided at a constant value and the area (A) changes. The relationship that determines output is $$\frac{V}{A}.$$

Accordingly, as the area, i.e., the field of view, changes, the output changes. Thus, a smaller field of view provides a larger energy to area ratio and a higher quality image. The use of this relationship can provide scalability to the ultrasonic imaging portion of the apparatus.

In an additional embodiment, a small field of view, i.e., one-inch field of view or less, can be translated over the object to be imaged to provide a field of view beyond that of the physical size of the transducer and/or detector size. For example, the ultrasonic source and the ultrasonic detector can be scanned in tandem in a raster-type scan or other suitable scan over the entire area to be imaged. Thus, the resulting image from the ultrasonic apparatus is a combination of the plurality of field of view images from the array. In addition, a smaller transducer with the attendant higher resolution, i.e., pixel to image ratio, can be used.

Figure 5:
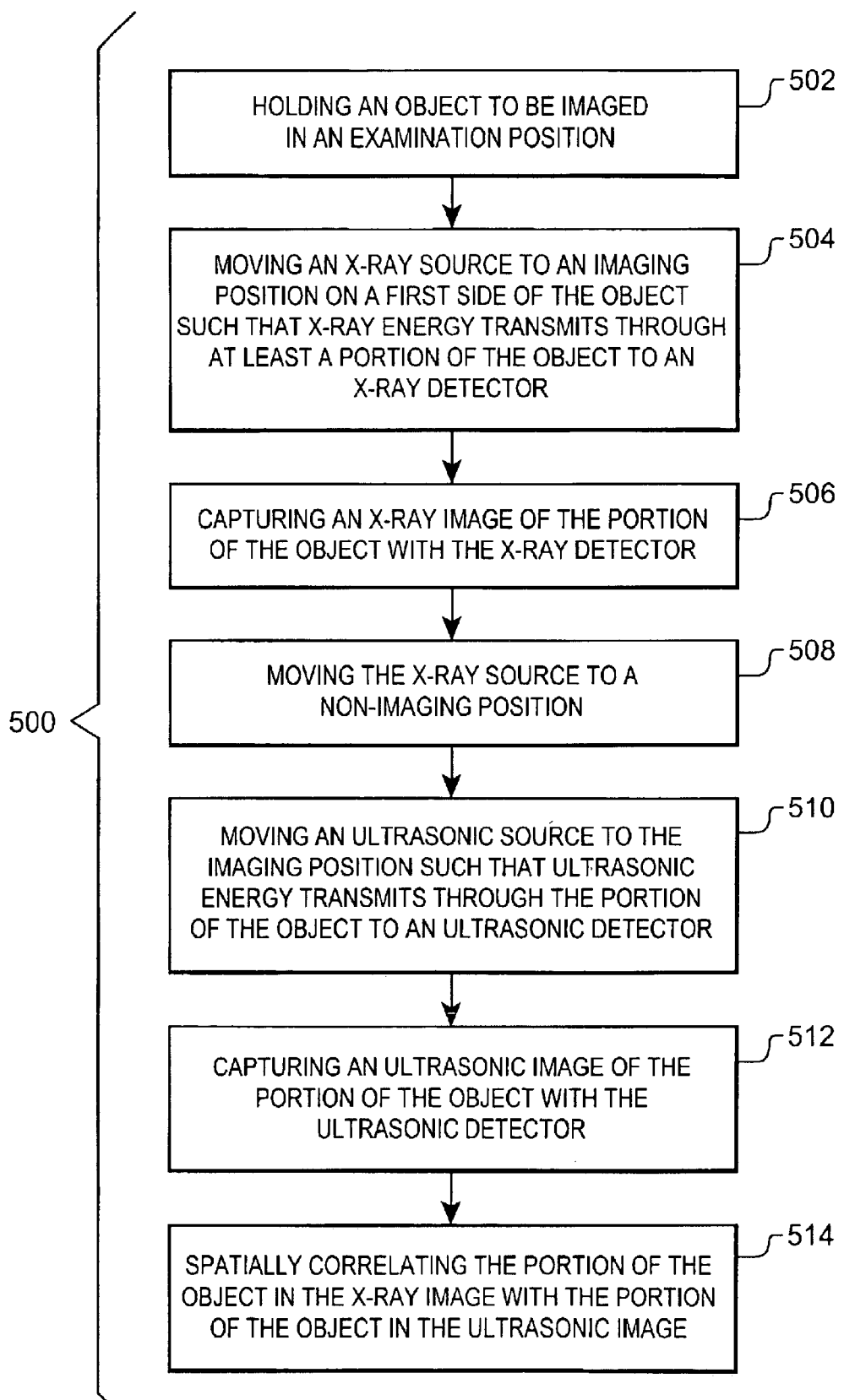
FIG. 5 is a flow diagram of a method of imaging an object with an apparatus for multi-mode imaging.

An exemplary method of imaging an object with an apparatus for multi-mode imaging is illustrated in FIG. 5 as method 500. The FIG. 5 method includes holding the object to be imaged in an examination position 502, moving an x-ray source to an imaging position on a first side of the object such that x-ray energy transmits through at least a portion of the object to an x-ray detector 504, capturing an x-ray image of the portion of the object with the x-ray detector 506, moving the x-ray source to a non-imaging position 508, moving an ultrasonic source to the imaging position such that ultrasonic energy transmits through the portion of the object to an ultrasonic detector 510, capturing an ultrasonic image of the portion of the object with the ultrasonic detector 512, and spatially correlating the portion of the object in the x-ray image with the portion of the object in the ultrasonic image 514.

In an exemplary examination position, the object is ultrasonically coupled to the ultrasonic source and the ultrasonic detector. Additionally, the object is held stationary in the examination position throughout the capturing of the x-ray image and the ultrasonic image. For example, the object can be compressed between opposing surfaces of a first plate and a second plate. In additional exemplary embodiments, the examination position can be a prone position of a patient in which the portion of the patient to be imaged, i.e., the object to be imaged, is rested in a particular position, or there are removable portions of the patient support element which provides access to the object to be imaged. Examples of prone supports are provided, for example, in U.S. Pat. No. 6,254,538 B1, the entire contents of which are herein incorporated by reference.

The x-ray images and the ultrasonic images each contain at least one registry object which can be used in spatially correlating the ultrasonic image and the x-ray image. The registry object can be within the field of view of the imaging apparatus during exposure and capturing of the object in an image, or it may be an electronically generated and/or depicted registry which is provided by the software which captures and manipulates the image or data. In additional exemplary method, the method calibrates a field of view of the x-ray source and a field of view of the ultrasonic source to result in spatially correlated images. In a still further exemplary method, the spatially correlated images are evaluated and a medical condition of the patient is diagnosed. For example, the object to be imaged can be a female breast, and the images can reveal cysts and/or other cancerous related tissue which can be the basis for a diagnosis of a condition of the patient.

By combining multiple exposure techniques using different energy sources with a stationary object to be imaged, a more comprehensive diagnosis may be performed with one compression of an object. Accordingly, the process of determining the exact location of any suspicious tissue growths within the object can be correlated and an appropriate diagnosis effected.

Figure 6A:
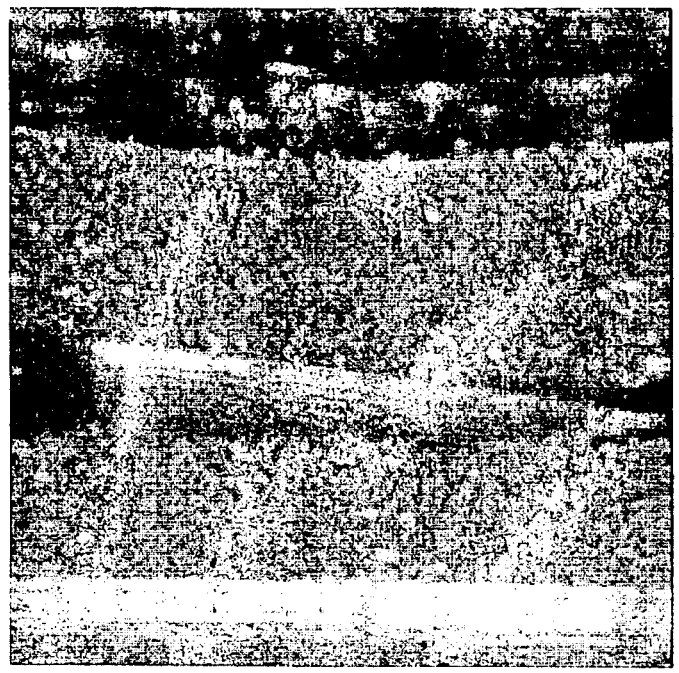
FIG. 6 shows a conventional ultrasonic image at FIG. 6A and a ultrasonic image consistent with the invention at FIG. 6B.
Figure 6B:
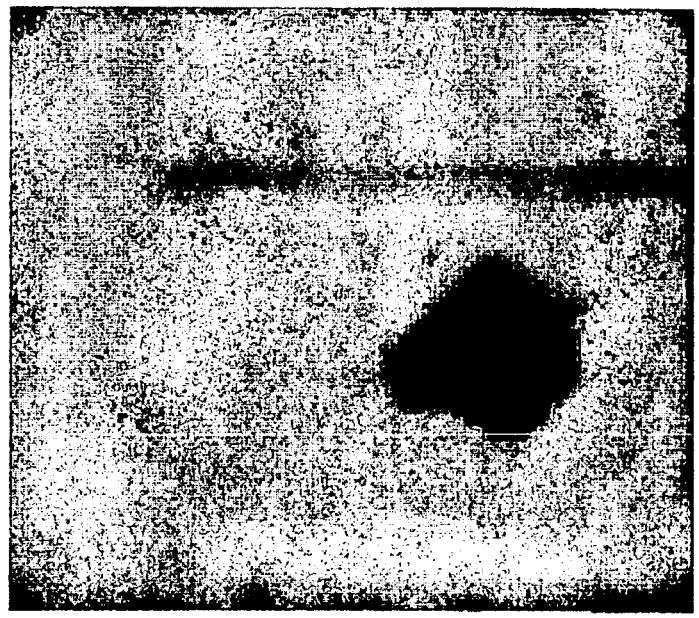

In an additional exemplary embodiment of the method, the ultrasonic imaging apparatus can be used in medical procedures to image a medical instrument in-situ, i.e., a biopsy needle, and/or a target of a medical procedure, such as an abnormality in a tissue. FIG. 6 shows an ultrasonic image in a conventional ultrasonic apparatus in FIG. 6A and an ultrasonic image in FIG. 6B consistent with the embodiments of the ultrasonic imaging apparatus described herein. The FIG. 6B image shows a resolved biopsy needle in a field of view with an abnormality in the tissue. Both the position of the biopsy needle and the abnormality are well resolved and substantially speckle-free. In contrast, the FIG. 6A image has substantial speckle and the biopsy instrument is poorly resolved, i.e., the position of the biopsy needle is difficult to determine due to the multi-plane nature of the conventional ultrasonic image.

Transmissive ultrasound can provide both resolution and spatial orientation of the medical instrument and/or the procedure target. This is because the resolution of the image in transmission mode does not depend on the angle of the reflective surfaces of the object being imaged as does reflection mode. In reflection mode, the relationship between the ultrasound source, orientation of the medical instrument and the ultrasound source is maintained within a narrow envelope so that reflected ultrasound propagates back to the detector. In contrast, in transmission mode, the relationship of source, instrument, and detector is broader, since a large array source and a large area detector can produce and detect the transmitted ultrasound. Further, exemplary embodiments of multimodal imaging with at least one mode being transmissive ultrasound can provide enhanced resolution, spatial orientation, and content and visual information.

In an exemplary embodiment, an apparatus for multimode imaging an object to obtain images in at least two ultrasonic imaging modes includes a first ultrasonic imaging transducer operating in a transmission mode and a second ultrasonic imaging transducer operating in a reflection mode, e.g., pulse echo or B-scan. The combination of transmission mode ultrasound and reflection mode ultrasound allows ultrasonic imagery from each mode to be collected on a common detector.

The apparatus can operate in two modes simultaneously. For example, the apparatus can operate in both a transmissive and a pulse echo mode. Transmissive mode provides indication of an object's acoustic attenuation and pulse echo mode provides information about an object's reflectivity. Thus, an object can appear dark in transmissive mode and light in pulse echo mode. Further, a pulse echo image distinguishes edges in features that are on the test object's surface. Combining transmissive imagery and pulse echo imagery provides an image with more content and visual information.

Figure 7:
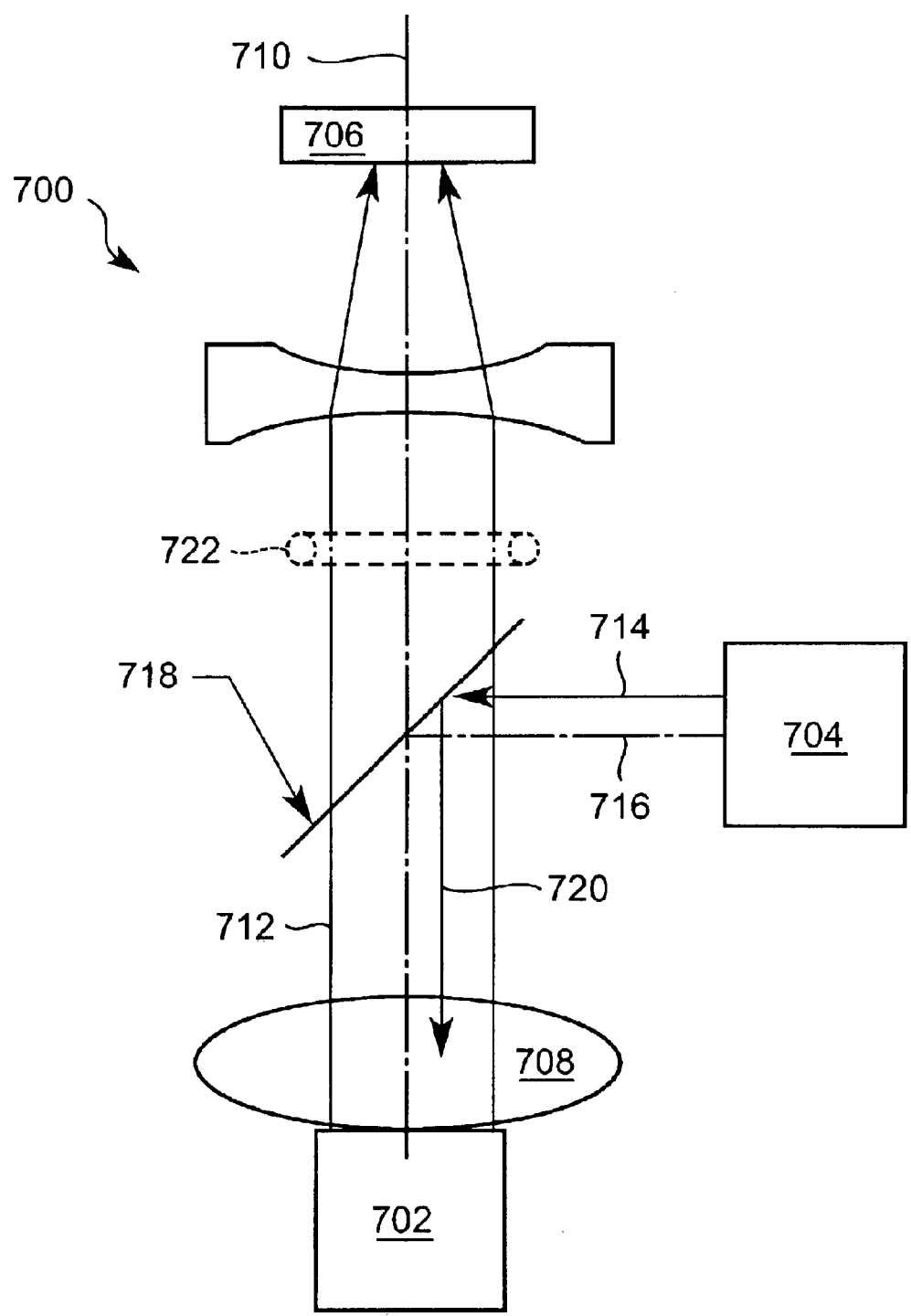
FIG. 7 shows an exemplary embodiment of an apparatus for multi-mode imaging of an object in which a first ultrasonic imaging apparatus is operating in a transmission mode.

For example, FIG. 7 shows an exemplary embodiment of an apparatus for multi-mode imaging of an object in which an ultrasonic imaging apparatus is combined with multiple ultrasonic imaging apparatus. The exemplary apparatus 700 comprises a first ultrasonic imaging transducer 702, a second ultrasonic imaging transducer 704, and an ultrasonic detector 706. The first ultrasonic imaging transducer 702, the second ultrasonic imaging transducer 704, and the ultrasonic detector 706 are arranged about an imaging area 708. The first ultrasonic imaging transducer 702 is colinear with the imaging area 708 and the ultrasonic detector 706 along a first beam axis 710 to transmit a first ultrasonic energy 712 from the first ultrasonic imaging transducer 702 through the imaging area 708 to the ultrasonic detector 706. The second ultrasonic imaging transducer 704 transmits a second ultrasonic energy 714 from the second ultrasonic imaging transducer 704 into the imaging area 708 along a second beam axis 716, the first beam axis 710 orthogonal to the second beam axis 716.

In one aspect, the second ultrasonic energy 714 is split by a beam splitter 718 and directed into the imaging area 708 and reflected to the ultrasonic detector 706. For example and as shown in the exemplary embodiment of FIG. 7, a beam splitter 718 is interposed between the ultrasonic detector 706 and the first ultrasonic imaging transducer 702. The beam splitter 718 acts to both reflect and transmit portions of the acoustic energy that falls upon it. A suitable beam splitter can be a thin piece of flat metal. Additional suitable beam splitters and additional information on ultrasonic equipment utilizing a beam splitter is disclosed in commonly owned U.S. patent application Ser. No. 09/479,598, entitled "ULTRASONIC IMAGER" and filed on Jan. 7, 2000, the entire contents of which are incorporated herein by reference.

In operation, a portion 720 of the acoustic energy from the second ultrasonic imaging transducer 704 is first reflected toward the imaging area 708 and upon interaction with an object in the imaging area 708, reflects toward the ultrasonic detector 706 passing through the beam splitter 718. Also, acoustic energy from the first ultrasonic imaging transducer 702 passes through the beam splitter 718 as the acoustic energy travels from the first ultrasonic imaging transducer 702 to the acoustic detector 706. When both the first ultrasonic imaging transducer 702 and the second ultrasonic imaging transducer 704 operate simultaneously, the ultrasonic detector 706 simultaneously receives a transmitted signal from the first ultrasonic imaging transducer 702 and a reflected signal from the second ultrasonic imaging transducer 704. Accordingly, a composite image from both modes can be developed or the transmission mode and the pulse echo mode can be alternated to collect information form each mode independently.

Although described herein with the use of a beam splitter, any suitable co-axial pulse echo beam can be used as a second ultrasonic source in the exemplary embodiment of FIG. 7. For example, the second ultrasonic imaging transducer can be colinear with the imaging area and the ultrasonic detector along the first beam axis to transmit a second ultrasonic energy from the second ultrasonic imaging transducer into the imaging area. Here, both the first ultrasonic energy and the second ultrasonic energy reflect to the ultrasonic detector.

In an exemplary embodiment, the second ultrasonic imaging transducer is an annular transducer located coaxially with the first ultrasonic source. As shown in FIG. 7, the annular transducer 722 can be used as an alternative to the second ultrasonic imaging transducer 7004. When operated in a pulse echo mode, the annular transducer 722 can generate ultrasonic imagery coaxially to the first beam axis 710 that can be detected commonly with the ultrasonic imagery of the first ultrasonic source 702 operating in transmission mode, e.g., by the first ultrasonic detector 706. The commonly collected ultrasonic imagery can then be combined or otherwise manipulated by an external device, such as a computer or a computer program.

Figure 8:
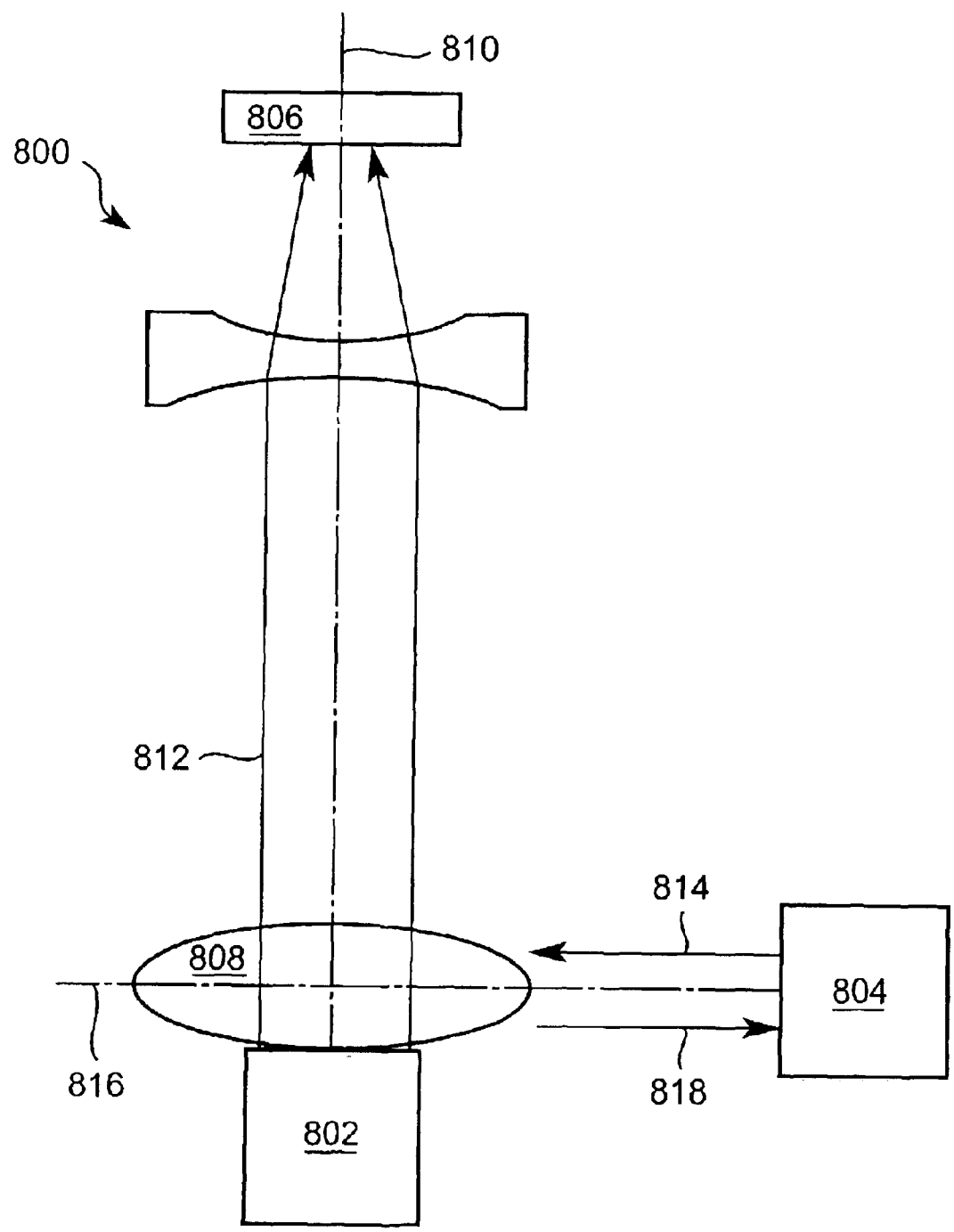
FIG. 8 shows an exemplary embodiment of an apparatus for multi-mode imaging of an object in which a first ultrasonic imaging apparatus is operating in a transmission mode.

FIG. 8 shows an exemplary embodiment of an apparatus for multi-mode imaging of an object in which an ultrasonic imaging apparatus is combined with multiple ultrasonic imaging apparatus. The exemplary apparatus 800 comprises a first ultrasonic imaging transducer 802, a second ultrasonic imaging transducer 804, and an ultrasonic detector 806. The first ultrasonic imaging transducer 802, the second ultrasonic imaging transducer 804, and the ultrasonic detector 806 are arranged about an imaging area 808. The first ultrasonic imaging transducer 802 is colinear with the imaging area 808 and the ultrasonic detector 806 along a first beam axis 810 to transmit a first ultrasonic energy 812 from the first ultrasonic imaging transducer 802 through the imaging area 808 to the ultrasonic detector 806. The second ultrasonic imaging transducer 804 transmits a second ultrasonic energy 814 from the second ultrasonic imaging transducer 804 into the imaging area 808 along a second beam axis 816, the first beam axis 810 orthogonal to the second beam axis 816.

The features of the exemplary embodiment of FIG. 8 can be substantially similar to those shown and described with respect to the exemplary embodiment of FIG. 7. However, in contrast to the exemplary embodiment of FIG. 7, in the exemplary embodiment of FIG. 8 the second ultrasonic energy 814 propagates directly into the imaging area 808 without a reorientation of the second beam axis 816, e.g., the propagation direction of the second ultrasonic energy 814 is not changed prior to the imaging area 808. The second ultrasonic imaging transducer 804 shown in FIG. 8 can, for example, operate in B-scan mode to obtain an ultrasonic image whose image plane is oriented parallel to the second beam axis 816 and perpendicular to the first beam axis 810. Accordingly, the ultrasonic image obtained in B-scan mode by the second ultrasonic imaging transducer 804 can be correlated to the ultrasonic image obtain in transmission mode by the first ultrasonic imaging transducer 802. Further, the second ultrasonic imaging transducer 804 can also detect ultrasonic energy, e.g., the reflected ultrasonic energy 818 by a suitable detector or a suitable transmitter/receiver for ultrasonic energy. When the second ultrasonic imaging transducer 804 also detects ultrasonic energy, the apparatus 800 includes a first ultrasonic detector located along the first beam axis and a second ultrasonic detector located along the second beam axis, the second ultrasonic imaging transducer being an ultrasonic transceiver operating in a B-scan mode to send and receive the second ultrasonic energy along the second beam axis.

Figure 9:
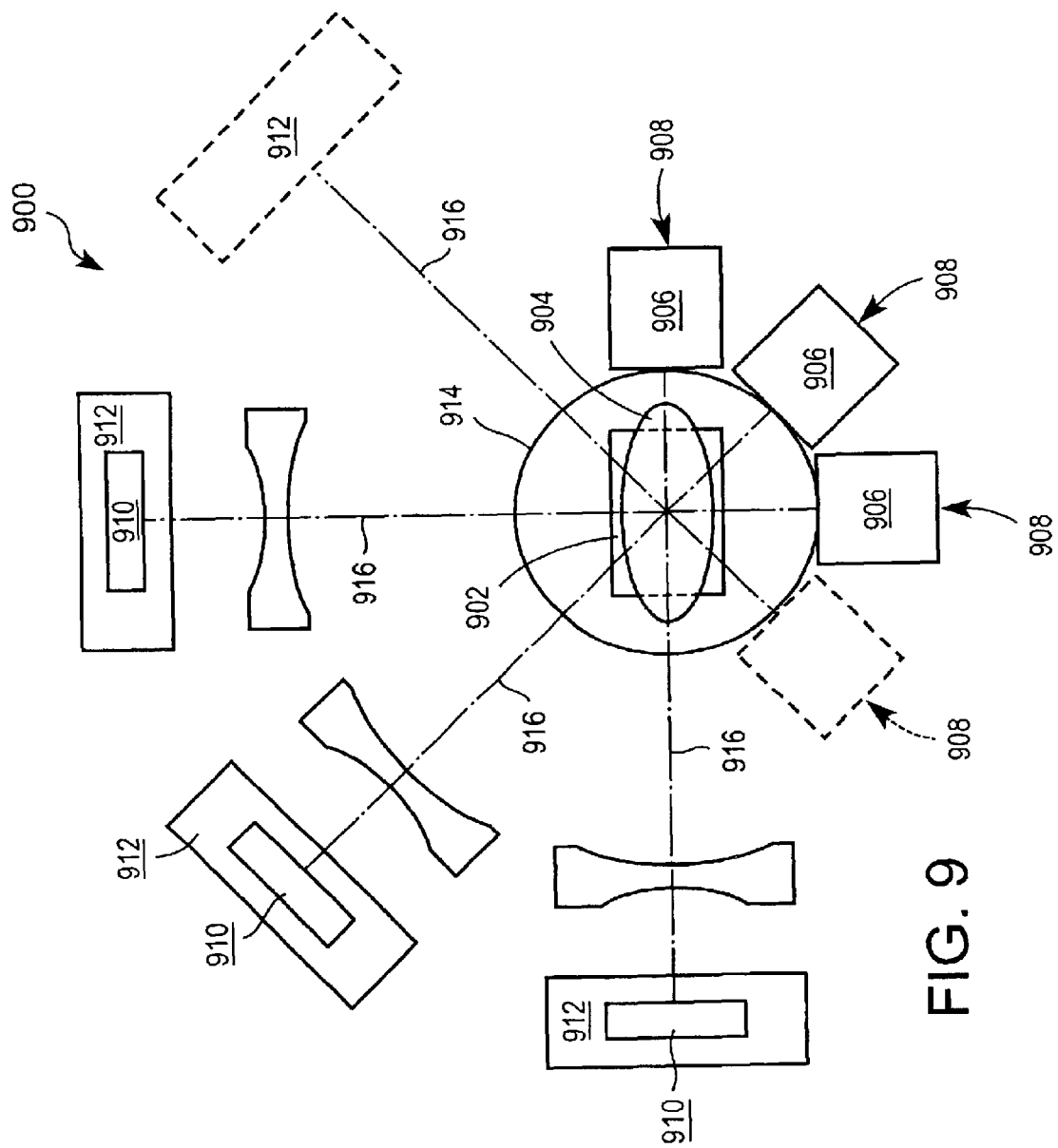
FIG. 9 shows an exemplary embodiment of an apparatus for multi-mode imaging of an object in which an ultrasonic imaging apparatus operating in a transmission mode is combined with multiple ultrasonic imaging apparatus operating in transmission mode.

FIG. 9 shows an exemplary embodiment of an apparatus for multi-mode imaging of an object in which an ultrasonic imaging apparatus is combined with multiple ultrasonic imaging apparatus. In the exemplary embodiment shown in FIG. 9, an apparatus 900 for multimode imaging an object from a plurality of imaging positions to obtain enhanced images, such as stereo images or orthogonal images or images with enhanced feature discrimination, comprises means for positioning an object 902 in an examination area 904, an ultrasonic source 906 for providing a plurality of imaging positions 908, an ultrasonic detector 910 for providing a plurality of detector positions 912 and an acoustic coupling 914 between the examination area 904, the ultrasonic source 906 and the ultrasonic detector 910. Each imaging position 908 is colinear with the examination area 904 and one of the plurality of detector positions 912 along a beam axis 916.

The means for positioning an object 902 can be any suitable means, such as a fixed or movable object stage, a plate, a cup, cuff, ring or receiving element that can receive an object to be imaged, such as a female breast, an arm, a portion of or the entire torso, or an animal, such as a small animal. The means for positioning an object can be enhanced by for example, vacuum or suction technology that assists in drawing the tissue into the means for positioning an object.

The acoustic coupling 914 can be any suitable acoustic coupling, such as a water bath or ultrasonic gel.

In one aspect, the ultrasonic source 906 can include a single ultrasonic source moveable between the imaging positions or a plurality of ultrasonic sources each positioned at a imaging position, or a combination thereof. For example, the single ultrasonic source can be repositioned sequentially to each of a plurality of imaging positions. The imaging positions can be either adjacent imaging positions, sequential imaging positions or imaging positions oriented in a predetermined pattern, such as imaging positions having a specified angular separation, e.g., 10°, 15°, 30°, 45°, 60°, 90°, and 180° of separation. Concurrently with the repositioning of the single ultrasonic source, a single ultrasonic detector can be repositioned to one of the detector positions such that the single ultrasonic source, the examination area, and the one detector position are colinear along the beam axis of the ultrasonic source. If more than one ultrasonic detector is used, repositioning may not be required or the frequency of repositioning may be reduced.

In another example, the ultrasonic sources 906 can include a plurality of ultrasonic sources. Each ultrasonic source can be located at a different one of the plurality of imaging positions. The plurality of imaging positions can have a specified angular separation, e.g., 10°, 15°, 30°, 45°, 60°, 90°, and 180° of separation, to obtain imagery from multiple angles about the examination area.

In another aspect, the ultrasonic detector 910 can include either a single ultrasonic detector moveable between the detector positions or a plurality of ultrasonic detectors each positioned at a detector position, or a combination thereof. Each of the plurality of ultrasonic detectors can be positioned at a different one of the detector positions such that each ultrasonic source, the examination area, and one of the plurality of ultrasonic detectors are colinear along the beam axis of the ultrasonic source.

In discussed herein, exemplary aspects of the apparatus for multimode imaging an object from a plurality of imaging positions produces an enhanced image by obtaining imagery, either simultaneously or sequently, from multiple angularly separated imaging positions about the examination area and reconstructing the imagery using conventional and commercially available imaging algorithms and software.

Although the present invention has been described in connection with several embodiments thereof, it will be appreciated by those skilled in the art that additions, deletions, modifications, and substitutions not specifically described may be made without department from the spirit and scope of the invention as defined in the appended claims.

What is claimed is:

1. An apparatus for multimode imaging of an object, comprising:
   means for holding an object to be imaged in compression in an examination area;
   a first ultrasonic source located on a first side of the examination area; and
   a first ultrasonic detector located on a second side of the examination area for receiving a first ultrasonic energy transmitted from the first ultrasonic source through the object,
   wherein the first ultrasonic source is movable from a first active position to a second inactive position, and the apparatus comprises a first x-ray source relocatable to the first active position and a first x-ray detector on the second side of the examination area.

2. The apparatus of claim 1, wherein the means for holding is a pair of ultrasonic transmissive plates.

3. The apparatus of claim 1, wherein the second side of the examination area is opposite the first side of the examination area.

4. The apparatus of claim 1, wherein the second side of the examination area is a side that receives a first x-ray energy generated by the first x-ray source and propagated transmissively through the object to the first x-ray detector.

5. The apparatus of claim 1, wherein the first ultrasonic detector captures an image from a plane within the object which is perpendicular to a beam axis extending from the first ultrasonic source to the first ultrasonic detector.

6. The apparatus of claim 1, wherein the first ultrasonic detector is an ultrasonic camera and the means for holding includes a feature that is transmissive to ultrasound.

7. The apparatus of claim 6, wherein the means for holding comprises a transducer and a lens of the ultrasonic camera.

8. The apparatus of claim 1, wherein the first ultrasonic source and the first ultrasonic detector are rotated about the examination area and a first beam axis between the first ultrasonic source and the first ultrasonic detector intersects at least a portion of the examination area.

9. An apparatus for multimode imaging of an object comprising:
   means for holding an object to be imaged in compression in an examination area;
   a first ultrasonic source located on a first side of the examination area;
   a first ultrasonic detector located on a second side of the examination area for receiving a first ultrasonic energy transmitted from the first ultrasonic source through the object; and
   at least a second ultrasonic source and a second ultrasonic detector, the second ultrasonic source located to received a second ultrasonic energy transmitted from the second ultrasonic source through the object,
   wherein a second beam axis between the second ultrasonic source and the second ultrasonic detector is angularly separated from a first beam axis between the first ultrasonic source and the first ultrasonic detector.

10. The apparatus of claim 9, wherein the means for holding is a pair of ultrasonic transmissive plates.

11. The apparatus of claim 9, wherein the second side of the examination area is opposite the first side of the examination area.

12. The apparatus of claim 9, wherein the first ultrasonic detector captures an image from a plane within the object which is perpendicular to a beam axis extending from the first ultrasonic source to the first ultrasonic detector.

13. The apparatus of claim 9, wherein the first ultrasonic detector is an ultrasonic camera and the means for holding includes a feature that is transmissive to ultrasound.

14. The apparatus of claim 13, wherein the means for holding comprises a transducer and a lens of the ultrasonic camera.

15. The apparatus of claim 9, wherein the first ultrasonic source and the first ultrasonic detector are rotated about the examination area and a first beam axis between the first ultrasonic source and the first ultrasonic detector intersects at least a portion of the examination area.

16. An apparatus for multimode imaging of an object, comprising:
   means for holding an object to be imaged in compression in an examination area;
   a first ultrasonic source located on a first side of the examination area;
   a first ultrasonic detector located on a second side of the examination area for receiving a first ultrasonic energy transmitted from the first ultrasonic source through the object;
   at least a second ultrasonic source operating in a pulse echo mode; and
   a beam splitter located in a first beam axis between the first ultrasonic source operating in a transmission mode and the first ultrasonic detector,
   wherein the second ultrasonic source transmits a second ultrasonic energy to the beam splitter in a direction orthogonal to the first beam axis and the second ultrasonic energy is split by the beam splitter and directed into the examination area.

17. The apparatus of claim 16, wherein the first ultrasonic detector simultaneously receives a transmitted signal from the first ultrasonic source and a reflected signal from the second ultrasonic source.

18. The apparatus of claim 16, wherein the means for holding is a pair of ultrasonic transmissive plates.

19. The apparatus of claim 16, wherein the second side of the examination area is opposite the first side of the examination area.

20. The apparatus of claim 16, wherein the first ultrasonic detector captures an image from a plane within the object which is perpendicular to a beam axis extending from the first ultrasonic source to the first ultrasonic detector.

21. The apparatus of claim 16, wherein the first ultrasonic detector is an ultrasonic camera and the means for holding includes a feature that is transmissive to ultrasound.

22. The apparatus of claim 21, wherein the holding means comprises a transducer and a lens of the ultrasonic camera.

23. The apparatus of claim 16, wherein the first ultrasonic source and the first ultrasonic detector are rotated about the examination area and a first beam axis between the first ultrasonic source and the first ultrasonic detector intersects at least a portion of the examination area.

24. An apparatus for multi-mode imaging of an object, comprising:
means for holding the object in an examination area;
an ultrasonic source;
an x-ray source;
means for mounting the ultrasonic source and the x-ray source, and for relocatably positioning either one of the ultrasonic source and the x-ray source at an imaging position on a first side of the examination area;
an ultrasonic detector located on a second side of the examination area for receiving ultrasonic energy transmitted from the ultrasonic source at the imaging position through the object; and
an x-ray detector located on the second side of the examination area for receiving x-ray energy transmitted from the x-ray source at the imaging position through the object.

25. The apparatus of claim 24, wherein the means for holding the object comprises a material that is transmissive to an ultrasonic energy generated by the ultrasonic source and to an x-ray energy generated by the x-ray source.

26. The apparatus of claim 24, wherein the means for holding the object is a pair of ultrasonic and x-ray transmissive plates.

27. The apparatus of claim 24, wherein the means for holding comprises a compressive means.

28. The apparatus of claim 24, wherein the second side of the examination area is opposite the first side of the examination area.

29. The apparatus of claim 24, wherein the ultrasonic detector captures an image from a plane within the object which is perpendicular to a path extending from the ultrasonic source to the ultrasonic detector.

30. The apparatus of claim 24, comprising a registry object in a field of view of the ultrasonic source and the x-ray source when each source is at the imaging position.

31. The apparatus of claim 30, wherein the registry object is a grid, at least one mark, at least one crosshair, or at least one aligning element.

32. The apparatus of claim 30, wherein the registry object is non-transmissive to both the ultrasonic energy and the x-ray energy.

33. The apparatus of claim 24, wherein the ultrasonic detector is an ultrasonic camera and the means for holding includes a camera including a feature that is transmissive to ultrasound.

34. The apparatus of claim 33, wherein the holding means comprises a transducer and a lens of the camera.

35. The apparatus of claim 24, wherein at least one of the ultrasonic source and the ultrasonic detector is moveable.

36. A method of multimode imaging an object with an apparatus to obtain images in at least two imaging modes, the method comprising:
holding an object to be imaged in an examination position;
moving an x-ray source to an imaging position on a first side of the object such that x-ray energy transmits through at least a portion of the object to an x-ray detector;
capturing an x-ray image of the portion of the object with the x-ray detector;
moving the x-ray source to a non-imaging position;
moving an ultrasonic source to the imaging position such that ultrasonic energy transmits through the portion of the object to an ultrasonic detector;
capturing an ultrasonic image of the portion of the object with the ultrasonic detector; and
spatially correlating the portion of the object in the x-ray image with the portion of the object in the ultrasonic image.

37. The method of claim 36, wherein, in the examination position, the object is compressed between opposing surface of a first plate and a second plate.

38. The method of claim 36, wherein, in the examination position, the object is ultrasonically coupled to the ultrasonic source and the ultrasonic detector.

39. The method of claim 36, wherein the object is held stationary in the examination position throughout the capturing of the x-ray image and the ultrasonic image.

40. The method of claim 36, wherein the x-ray image and the ultrasonic image each contain at least one registry object used in spatially correlating the ultrasonic image and the x-ray image.

41. The method of claim 36, comprising evaluating the spatially correlated images and diagnosing a medical condition.

42. The method of claim 36, comprising calibrating a field of view of the x-ray source and a field of view of the ultrasonic source to result in the spatially correlated images.

43. The method of claim 36, wherein the object to be imaged is a female breast, an arm, a portion of or the entire torso, or an animal.

44. The method of claim 36, wherein the object to be imaged is a female breast.

45. An apparatus for multimode imaging an object to obtain images in at least two ultrasonic imaging modes, the apparatus comprising:
a first ultrasonic imaging transducer;
a second ultrasonic imaging transducer; and
an ultrasonic detector;
wherein the first ultrasonic imaging transducer, the second ultrasonic imaging transducer, and the ultrasonic detector are arranged about an imaging area,
wherein the first ultrasonic imaging transducer is colinear with the imaging area and the ultrasonic detector along a first beam axis to transmit a first ultrasonic energy from the first ultrasonic imaging transducer through the imaging area to the ultrasonic detector, and
wherein the second ultrasonic imaging transducer transmits a second ultrasonic energy from the second ultrasonic imaging transducer into the imaging area along a second beam axis, the first beam axis orthogonal to the second beam axis.

46. The apparatus of claim 45, including a beam splitter, wherein the second ultrasonic energy interacts with the beam splitter to propagate at least a portion of the second ultrasonic energy coaxially to the first ultrasonic energy into the imaging area and the second ultrasonic energy reflects to the ultrasonic detector.

47. The apparatus of claim 45, including a beam splitter, wherein the second ultrasonic energy is split by the beam splitter and directed into the imaging area and reflected to the ultrasonic detector.

48. The apparatus of claim 45, wherein the second ultrasonic imaging transducer is directly ultrasonically coupled to the imaging area.

49. The apparatus of claim 45, wherein the ultrasonic detector is an ultrasonic camera.

50. The apparatus of claim 45, wherein the ultrasonic detector simultaneously receives a transmitted signal from the first ultrasonic imaging transducer and a reflected signal from the second ultrasonic imaging transducer.

51. The apparatus of claim 45, wherein the ultrasonic detector includes a first ultrasonic detector located along the first beam axis and a second ultrasonic detector located along the second beam axis.

52. The apparatus of claim 45, wherein the second ultrasonic imaging transducer is an ultrasonic transceiver and operates in a B-scan mode to send and receive the second ultrasonic energy along the second beam axis.

53. An apparatus for multimode imaging an object to obtain images in at least two ultrasonic imaging modes, the apparatus comprising: a first ultrasonic imaging transducer operating in a transmission mode; a second ultrasonic imaging transducer operating in a pulse echo mode; and an ultrasonic detector; wherein the first ultrasonic imaging transducer, the second ultrasonic imaging transducer, and the ultrasonic detector are arranged about an imaging area, wherein the first ultrasonic imaging transducer is colinear with the imaging area and the ultrasonic detector along a first beam axis to transmit a first ultrasonic energy from the first ultrasonic imaging transducer through the imaging area to the ultrasonic detector, and wherein the second ultrasonic imaging transducer is colinear with the imaging area and the ultrasonic detector along the first beam axis to transmit a second ultrasonic energy from the second ultrasonic imaging transducer into the imaging area, the second ultrasonic energy reflected to the ultrasonic detector.

54. The apparatus of claim 53, wherein the second ultrasonic imaging apparatus includes an annular transducer.

55. An apparatus for multimode imaging an object from a plurality of imaging positions, the apparatus comprising: means for positioning an object in an examination area; an ultrasonic source for providing a plurality of imaging positions; an ultrasonic detector for providing a plurality of detector positions; and an acoustic coupling between the examination area, the ultrasonic source and the ultrasonic detector, wherein each imaging position is colinear with the examination area and one of the plurality of detector positions along a beam axis.

56. The apparatus of claim 55, wherein the ultrasonic source is a single ultrasonic source, the single ultrasonic detector repositioned to each of the plurality of imaging positions.

57. The apparatus of claim 56, wherein the single ultrasonic source is repositioned sequentially to each of the plurality of imaging positions.

58. The apparatus of claim 56, wherein the ultrasonic detector is a single ultrasonic detector, the single ultrasonic detector repositioned concurrent with the repositioning of the single ultrasonic source to one of the detector positions such that the single ultrasonic source, the examination area, and the one detector position are colinear along the beam axis of the ultrasonic source.

59. The apparatus of claim 56, wherein the ultrasonic source is a plurality of ultrasonic sources, each ultrasonic source located at a different one of the plurality of imaging positions.

60. The apparatus of claim 59, wherein the ultrasonic detector is a plurality of ultrasonic detectors, each of the plurality of ultrasonic detectors positioned at a different one of the detector positions.

61. The apparatus of claim 55, wherein the apparatus produces an enhanced image.

62. The apparatus of claim 61, wherein the enhanced image is a stereo image or an orthogonal image.

* * * * *